(12) United States Patent
Fujita

(10) Patent No.: US 7,034,002 B1
(45) Date of Patent: Apr. 25, 2006

(54) ANGIOTENSIN CONVERTING ENZYME INHIBITOR

(75) Inventor: Hiroyuki Fujita, Ibaraki (JP)

(73) Assignee: The Nippon Synthetic Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 09/663,709

(22) Filed: Sep. 18, 2000

(30) Foreign Application Priority Data

Oct. 15, 1999 (JP) .............................. 11/293113

(51) Int. Cl.
*A61K 38/04* (2006.01)

(52) U.S. Cl. .......................... 514/15; 514/16; 514/17; 514/18; 514/19; 514/20; 530/328; 530/329; 530/330; 530/331; 435/70.1

(58) Field of Classification Search .................. 514/15, 514/16, 17, 18, 19, 21, 20; 530/328, 329, 530/330, 331; 435/70.1
See application file for complete search history.

(56) References Cited

U.S. PATENT DOCUMENTS 5,314,807 A    5/1994 Yoshikawa et al. ........ 435/68.1
5,369,015 A  * 11/1994 Yoshikawa et al. ........ 435/68.1

FOREIGN PATENT DOCUMENTS

JP         6-298794     * 10/1994

OTHER PUBLICATIONS

Yokoyama et al. "Peptide Inhibitors for Angiotensin I-Converting Enzyme From Thermolysin Digest of Dried Bonito." Biosci. Biotech. Biochem. vol. 56, No. 10, pp. 1541-1545, 1992.*

Patent Abstracts of Japan, vol. 016, No. 273 (C-0953), Jun. 18, 1992 & 04069398 A (Nippon Synthetic Chemind Co. Ltd: The), Mar. 4, 1992.*

File Caplus on Stn. Dn No. 123:65813. JP 06340692, Dec. 13, 1994. Abstract date 1995. Abstract only.*

"Peptide Inhibitors for Angiotensin I-Converting Enzyme from Thermolysin Digest of Dried Bonito" Bioscience Biotechnology, Biochemistry, Japan Soc. for Bioscience, Biotechnology and Agrochem. Tokyo, JP, vol. 56, No. 10, 1992, pp. 1541-1545, XP000973744.

Patent Abstracts of Japan, vol. 1995, No. 01, Feb. 28, 1995 & JP 06 298794 A (Nippon Synthetic Chemind Co Ltd: The), Oct. 25, 1994.

Patent Abstracts of Japan, vol. 016, No. 411 (C-0979), Aug. 31, 1992 & JP 04 139196 A (Nippon Synthetic Chemind Co Ltd: The), May 13, 1992.

Patent Abstracts of Japan, vol. 016, No. 273 (C-0935), Jun. 18, 1992 & JP 04 069398 A (Nippon Synthetic Chemind Co Ltd: The), Mar. 4, 1992.

"LKPNM: a prodrug-type ACE-inhibitory peptide derived from fish protein" Immunopharmacology, Elsevier Science Publishers BV, XX, vol. 44, Oct. 15, 1999, pp. 123-127, XP000973860.

* cited by examiner

*Primary Examiner*—Anish Gupta
(74) *Attorney, Agent, or Firm*—Armstrong, Kratz, Quintos, Hanson & Brooks, LLP

(57) ABSTRACT

The present invention provides an angiotensin converting enzyme inhibitor having strong activity of inhibiting angiotensin converting enzyme, good hue and easily to take in which is a composition containing peptides obtained by digesting a fish meat with thermolysin enzyme, and wherein a content of a polypeptide ingredient having a molecular weight of at least 5000 is at most 10% by weight.

3 Claims, No Drawings

SEQUENCE LISTING

```
<160> NUMBER OF SEQ ID NOS: 14

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
 1               5                   10

<210> SEQ ID NO 2
<211> LENGTH: 2
<212> TYPE: PRT
<213> ORGANISM: mammal, fish, crustaceans

<400> SEQUENCE: 2

Ile Tyr
 1

<210> SEQ ID NO 3
```

```
<211> LENGTH: 3
<212> TYPE: PRT
<213> ORGANISM: mammal, fish, crustaceans

<400> SEQUENCE: 3

Phe Gln Pro
 1

<210> SEQ ID NO 4
<211> LENGTH: 3
<212> TYPE: PRT
<213> ORGANISM: mammal, fish, crustaceans

<400> SEQUENCE: 4

Ile Leu Tyr
 1

<210> SEQ ID NO 5
<211> LENGTH: 3
<212> TYPE: PRT
<213> ORGANISM: mammal, fish, crustaceans

<400> SEQUENCE: 5

Ile Tyr Ala
 1

<210> SEQ ID NO 6
<211> LENGTH: 3
<212> TYPE: PRT
<213> ORGANISM: mammal, fish, crustaceans

<400> SEQUENCE: 6

Ile Lys Trp
 1

<210> SEQ ID NO 7
<211> LENGTH: 4
<212> TYPE: PRT
<213> ORGANISM: mammal, fish, crustaceans

<400> SEQUENCE: 7

Leu Lys Tyr Pro
 1

<210> SEQ ID NO 8
<211> LENGTH: 4
<212> TYPE: PRT
<213> ORGANISM: mammal, fish, crustaceans

<400> SEQUENCE: 8

Ile Val Arg Asp
 1

<210> SEQ ID NO 9
<211> LENGTH: 5
<212> TYPE: PRT
<213> ORGANISM: mammal, fish, crustaceans

<400> SEQUENCE: 9

Leu Lys Pro Asn Met
 1               5

<210> SEQ ID NO 10
<211> LENGTH: 5
<212> TYPE: PRT
```

-continued

```
<213> ORGANISM: mammal, fish, crustaceans

<400> SEQUENCE: 10

Ile Trp His His Thr
 1               5

<210> SEQ ID NO 11
<211> LENGTH: 5
<212> TYPE: PRT
<213> ORGANISM: mammal, fish, crustaceans

<400> SEQUENCE: 11

Ala Leu Pro His Ala
 1               5

<210> SEQ ID NO 12
<211> LENGTH: 6
<212> TYPE: PRT
<213> ORGANISM: mammal, fish, crustaceans

<400> SEQUENCE: 12

Ile Lys Pro Leu Asn Tyr
 1               5

<210> SEQ ID NO 13
<211> LENGTH: 6
<212> TYPE: PRT
<213> ORGANISM: mammal, fish, crustaceans

<400> SEQUENCE: 13

Asp Tyr Gly Leu Tyr Pro
 1               5

<210> SEQ ID NO 14
<211> LENGTH: 9
<212> TYPE: PRT
<213> ORGANISM: mammal, fish, crustaceans

<400> SEQUENCE: 14

Ile Val Gly Arg Pro Arg His Gln Gly
 1               5
```

ANGIOTENSIN CONVERTING ENZYME INHIBITOR

BACKGROUND OF THE INVENTION

The present invention relates to an angiotensin converting enzyme inhibitor comprising a composition containing peptide obtained by digesting fish meat with thermolysin enzyme, which can be useful for medical supplies, foods, health foods, specified foods for health care and the like.

Angiotensin converting enzyme is an enzyme which is chiefly present in the lung, vascular endothelial cells and renal proximal tubules and acts on angiotensin I (Asp-Arg-Val-Tyr-Ile-His-Pro-Phe-His-Leu (SEQ. ID. NO. 1)) to cleave a dipeptide (His9-Leu10) off its C-terminus to give rise to angiotensin II which has potent pressor activity. Futhermore, this enzyme decomposes bradykinin, a physiological hypotensive substance, to inactivate it and, as such, is intimately involved in the pressor system. It has been considered that inhibition of angiotensin converting enzyme would lower the blood pressure and is, therefore, clinically useful for the prevention and treatment of hypertension.

Recently, since captopril, a proline derivative, was synthesized and found to have hypotensive activity, much research has been undertaken for synthesizing a variety of angiotensin converting enzyme inhibitors and it has also been attempted to isolate such substances from natural resources.

This is because natural type angiotensin converting enzyme inhibitors available from foods or food materials may be expected to be of value as antihypertensive agents of low toxicity and high safety.

The present inventor has already disclosed a novel peptide which contains Leu-Lys-Pro backbone in Japanese Unexamined Patent Application Publication No. 69397/1992. In Japanese Unexamined Patent Application Publication No. 144696/1992, there is disclosed the method of producing a composition having an angiotensin converting enzyme inhibitor which is obtained by hydrolyzing a protein with a thermolysin. Furthermore, in Japanese Unexamined Patent Application Publication No. 244979/1993, there is disclosed a method of producing a composition having an angiotensin converting enzyme inhibitors which is obtained by hydrolyzing the residue mainly comprising water-insoluble protein with a protease after heat-treating meat in water of not less than 50° C. to exclude water-soluble protein by extraction.

However, though an inhibiting activity of novel peptides disclosed in the above-mentioned Japanese Unexamined Patent Publication No. 69397/1992 is very strong, it takes much effort and higher cost to separate the peptide in practice. Also, though a composition having relatively high inhibitory activity is obtained by those methods disclosed in Japanese Unexamined Patent Application Publication No. 144696/1992 and Japanese Unexamined Patent Application Publication No. 244979/1993, a taken amount of the composition is slightly increased in order to obtain effect. Therefore, it is desired that a taken amount be further reduced in order to take the composition readily every day. Furthermore, if dried bonito is used as protein, the above compositions are still open to improvements in an aftertaste though peptide-specific bitterness is reduced.

SUMMARY OF THE INVENTION

As a result of making an intensive study in order to solve the above problems, the present inventors have found the followings and completed the present invention. They have found that an angiotensin converting enzyme inhibitor (hereinafter referred to as "inhibitor") comprises a peptide containing composition obtained by digesting fish meat with thermolysin enzyme whose content of a polypeptide element having a molecular weight of at least 5000 is at most 10% by weight. They have also found that the inhibitor has excellent inhibitory activity, good hue, no bitterness and nice aftertaste and is easy to be taken.

That is to say, the present invention relate to an angiotensin converting enzyme inhibitor, which is a composition containing peptides obtained by digesting fish meat with thermolysin enzyme, whose a content of a polypeptide ingredient having a molecular weight of at least 5000 is at most 10% by weight.

In the above-mentioned inhibitor, the composition is preferably containing peptides comprises at least one selected from the group consisting of
Ile-Tyr (SEQ. ID. NO. 2),
Phe-Gln-Pro (SEQ. ID. NO. 3),
Ile-Leu-Tyr (SEQ. ID. NO. 4),
Ile-Tyr-Ala (SEQ. ID. NO. 5),
Ile-Lys-Trp (SEQ. ID. NO. 6),
Leu-Lys-Tyr-Pro (SEQ. ID. NO. 7),
Ile-Val-Arg-Asp (SEQ. ID. NO. 8),
Leu-Lys-Pro-Asn-Met (SEQ. ID. NO. 9),
Ile-Trp-His-His-Thr (SEQ. ID. NO. 10),
Ala-Leu-Pro-His-Ala (SEQ. ID. NO. 11),
Ile-Lys-Pro-Leu-Asn-Tyr (SEQ. ID. NO. 12),
Asp-Tyr-Gly-Leu-Tyr-Pro (SEQ. ID. NO. 13), and
Ile-Val-Gly-Arg-Pro-Arg-His-Gln-Gly (SEQ. ID. NO. 14).

In the above-mentioned inhibitor, the fish meat is preferably a dried fish.

In the above-mentioned inhibitor, the fish meat is preferably a residue from extraction of the dried fish with boiled water.

In the above-mentioned inhibitor, the dried fish is preferably a dried bonito.

DETAILED DESCRIPTION

The present invention is explained in detail as follows.

The composition containing a peptide according to the present invention can be obtained by digesting fish meat with thermolysin. Examples of fish meat are raw meat of skipjack, mackerel, sardine, cod, salmon, pacific saury, young yellowtail, horse mackerel, dried meat thereof, the residue thereof which is extracted by hot water, dried fish meat obtained by drying the extracted residue or occasionally by putting mold thereto, and residue of the dried fish meat extracted by hot water. Preferably, residue of the dried fish meat extracted by hot water is used. Also, dried bonito is preferably used among the above dried fish meat.

A thermolysin enzyme as resolution enzyme may be purified enzyme solution, mixed enzyme solution of a few other enzymes or market solution such as "Thermoase" (available from Daiwa Kasei K. K.).

When fish meat is digested with a thermolysin enzyme, the fish meat is hydrolyzed by adding water and thermolysin enzyme thereto. In the hydrolysis, fish meat can be pretreated owing to its property, and in that case, water or hot water is added to the fish meat, and then mixing and strong homogenization is carried out. Amount of thermolysin enzyme preferably ranges from 0.05 to 5.0% by weight, more preferably from 0.1 to 1.0% by weight to the total of an amount of fish meat and water. A thermolysin enzyme amount of less than 0.05% by weight is not preferable because it will fail to promote enough hydrolysis. Also, a thermolysin enzyme amount of more than 5.0% by weight is not preferable because thermolysin enzyme will be only wasted.

Reaction temperature of hydrolysis preferably ranges from 10 to 85° C., more preferably, from 40 to 80° C. A reaction temperature of lower than 10° C. is not preferable because it will fail to promote enough hydrolysis. Also, a reaction temperature of over 85° C. is not preferable because inhibitory activity of thermolysin enzyme will be badly damaged.

A pH of hydrolysis preferably ranges from 6 to 8. A pH of less than 6 or over 8 is not preferable because a hydrolysis rate will be lowered. Since a solution before the beginning of hydrolysis reaction generally has a pH of 4 to 5.5, it is preferable to adjust a pH to 6 to 8 by using an alkaline solution (such as sodium chloride solution).

A reaction period preferably ranges from 10 minutes to 30 hours, more preferably, from 3 to 20 hours. A reaction period of shorter than 10 minutes is not preferable because a collecting rate of the digested compound becomes low. Also, a reaction period of longer than 30 hours is not preferable because production efficiency will be lowered.

Though a hydrolysis ratio is not particularly limited, final hydrolysis ratio is preferably adjusted to from 10 to 60%, and more preferably, from 20 to 50%. A hydrolysis ratio of lower than 10% is not preferable because little peptide will be obtained. Also, a hydrolysis ratio of higher than 60% is not preferable because hydrolysis has to be continued for a long time and a large amount of thermolysin enzyme is required to obtain a ratio of 60%. The hydrolysis ratio can be measured in accordance with a method on Journal of Agriculture and Food Chemistry, vol. 24, no. 6, pages 1090 to 1093 (1976).

The characteristic of the present invention is that a content of polypeptide having a molecular weight of at least 5000 which is included in the peptide-containing composition obtained by dissolution with the above enzyme is not more than 10% by weight to the solid portion of the composition. Specifically, from the above digested composition containing 15 to 30% by weight of peptide having a molecular weight of 5000, the peptide having a molecular weight of 5000 will be removed so that a content of the peptide having a molecular weight of 5000 is at most 10% by weight, more preferably from 0.1 to 5% by weight. It is not suitable when a content of the peptide having a molecular weight of 5000 is over 10% by weight, because there are defects that hue will become yellow or brown, bitterness slightly remains to give unnatural flavor, and that aftertaste remains for a long time if the peptide is added to weak-flavored things, and further because inhibitory activity will not be improved.

In the present invention, molecular weight of the sample is measured by a gel filtration chromatography. Concretely, using a peptide and a protein [Asp-Gly-Leu-Tyr-Pro (molecular weight 563), neurotensin (molecular weight 1637), ribonuclease (molecular weight 13700) as s standard substance, which have the known molecular weights, an extract is eluted in the following conditions to determine a retention time, and a molecular weight is determined by using a calibration curve obtained by plotting the molecular weights on the ordinate and the retention times on the abscissa logarithmically. In the invention, also an amount "% by weight" of the components having a molecular weight of at least 5000 is represented as "% area" of the peaks corresponding to components having a molecular weight of at least 5000 after dividing the peaks at the position of the molecular weight 5000 on an elution chromatogram.

(Fraction Conditions)
Column: Protein Pak60 (made by Waters) 5×250 mm
Mobile phase: 50% by volume acetonitrile aqueous solution containing 0.1% by volume TFA (trifluoroacetic acid)
Flow rate: 0.7 mL/min
Detection: RI
Sample amount: 1 mg (Relation Between Molecular Weight of Standard Substance and Elution Time)

| Standard substance | Molecular weight | Elution time (minute) |
|---|---|---|
| Asp-Gly-Leu-Tyr-Pro | 563 | 31 |
| Neurotensin | 1637 | 26 |
| Ribonuclease | 13700 | 19 |

In the above-mentioned conditions, since a substance having a molecular weight of 5000 is eluted at 29 minutes, any substance eluted at not more than 29 minutes is regarded as polypeptide components having a molecular weight of at least 5000.

The followings are examples of a method for removing a polypepitde component having a molecular weight of at least 5000.

[1] a method for removing fractions having a molecular weight of at least 5000 by means of a gel filtration chromatography

[2] a method for removing fractions having a molecular weight of at least 5000 by means of a membrane treatment

[31 a method for removing fractions having a high molecular weight by a solvent extraction using a polar organic solvent such as methanol, ethanol, propanol, butanol, chloroform, ethyl acetate, toluene, hexane or benzene These methods can be used solely or in a combination use of two or more thereof.

The methods [1] to [31 are explained briefly.

In the method [1], the procedure described above as a molecular weight analysis is performed in an industrial scale.

In the method [2], an extract is filtered through a membrane having a fractionation molecular weight of about 5000 (UF membrane), such as UF membrane "PLCC (fractionation molecular weight 5000)" available from Millipore, UF membrane "AES-5 (fractionation molecular weight 5000)" available from Advanced Membrane Technology, UF membrane "HFK-131 (fractionation molecular weight 5000)" available from Abco, and UF membrane "SEP1013 (fractionation molecular weight 3000)" available from Asahi Chemical Industry Co., Ltd.

In the method [3], an extract is concentrated to such an extent that no precipitation appears, organic solvent concentration within the system is 60 to 99% by volumes, by addition of 5 to 100 volumes of organic solvent thereto to precipitate any substance having a high molecular weight.

The obtained inhibitor of the present invention is a mixture of various oligopeptides, some nucleic acid and protein which is partly digested, and as the oligopeptide, at least one of the following peptides is contained:
Ile-Tyr (SEQ. ID. NO. 2),
Phe-Gin-Pro (SEQ. ID. NO. 3),
Ile-Leu-Tyr (SEQ. ID. NO. 4),
Ile-Tyr-Ala (SEQ. ID. NO. 5),
Ile-Lys-Trp (SEQ. ID. NO. 6),
Leu-Lys-Tyr-Pro (SEQ. ID. NO. 7), Ile-Val-Arg-Asp (SEQ. ID. NO. 8),
Leu-Lys-Pro-Asn-Met (SEQ. ID. NO. 9),
Ile-Trp-His-His-Thr (SEQ. ID. NO. 10),
Ala-Leu-Pro-His-Ala (SEQ. ID. NO. 11),
Ile-Lys-Pro-Leu-Asn-Tyr (SEQ. ID. NO. 12),
Asp-Tyr-Gly-Leu-Tyr-Pro (SEQ. ID. NO. 13), and
Ile-Val-Gly-Arg-Pro-Arg-His-Gln-Gly (SEQ. ID. NO. 14).

The above Leu is leucine, Lys lysine, Pro proline, Asn asparagine, Met methionine, Ile isoleucine, Trp tryptophan, Phe phenylalanine, Gln glutamine, Tyr tyrosine, Gly glycine, His histidine, Thr threonine, Ala alanine, Val valine, Arg arginine and Asp aspartic acid. All the above amino acid of the present invention is L-isomer.

The inhibitor of the present invention is a powder produced by preparing digested solution obtained by hydrolysis having the above composition after removing a solution or water. As a dehydration method, there are employed concentration drying, freeze drying, spray drying, vacuum drying and the like. The inhibitor of the present invention is used as pharmaceuticals and health foods (health supplement foods) in the form of a preparation, or is added to food products as it is.

The peptides according to the present invention are generally administered as formulated with pharmaceutical carriers and excipients, which are commonly used in the pharmaceutical industry and inert to the peptides of the invention. Among such carriers and excipients are lactose, glucose, mannitol, dextrin, cyclodextrin, starch, sucrose, magnesium metasilicate aluminate, synthetic aluminum silicate, carboxymethylcellulose sodium, hydroxypropylstarch, carboxymethylcellulose calcium, ion exchange resins, methylcellulose, gelatin, gum arabic, hydroxypropylcellulose, hydroxypropylmethylcellulose, polyvinylpyrrolidone, polyvinyl alcohol, soft silicic anhydride, magnesium stearate, talc, tragacanth, bentonite, B gum, titanium dioxide, sorbitan fatty acid esters, sodium lauryl sulfate, glycerol, glycerol fatty acid ester, purified lanolin, glycerogelatin, polysorbate, macrogols, vegetable oils, waxes, liquid paraffin, white vaseline, fluorocarbons, nonionic surfactants, propylene glycol, water and the like.

The dosage form may be a tablet, capsule, granule, powder, syrup, suspension or injectable solution. These preparations can be manufactured the established pharmaceutical procedures.

The medicament or health food prepared above is used for the purpose of preventing blood pressure depression, myocardial enlargement and apoplexy.

Also, since the inhibitor of the present invention has little bitterness and good aftertaste, it can be used for foods such as processed agricultural or marine foods, milk products, confectionery sweets, seasonings, drinks, freeze-dry foods and retort-packed foods, health foods, health supporting foods or food additives.

An inhibitor of the present invention can be added to a food product as the following without any specific limitation.

(1) Processed Agricultural and Marine Products gelatin noodle, pureed sweet red-bean jam, a gelatinous food made from devil's-tongue starch, bread, noodles (instant noodle, pasta, raw noodle, dried noodle), rice cake, cereals, processed soybean products (tofu, soybean milk, natto, dried bean curd), processed marine products [boiled fish paste, (crab-flavored) fish string sausages, (fish) ham, (fish) sausage, (fish) wieners, rice topping, layer flakes for rice with tea], canned foods (canned tuna, oil-preserved sardines, yakitori skewers), retort-packed foods (curry, stew, spaghetti sause)

(2) Dairy Products milk, processed milk, lactic fermented beverage, butter, cheese, condensed milk, powdered milk (3) Confectionery cake, mousse, (powdered) dessert, ice cream, candy, chocolate, gumdrop, cookie, wafer, jelly (4) Seasoning miso(fermented soybean paste), soy sauce, flavoring and seasoning, (powdered) natural seasoning, sauce, dressing, barbecue sauce, sweet sake seasoning, curry, stew, hot and mild spice, yogurts (5) Beverage Refreshing beverage (carbonated beverage, fruit juice, sport supplement beverage, health drink), luxury beverage (coffee, cocoa drink, barley beverage), miso soup, clear soup (6) Health Foods 1] food containing Saponin (food containing Panax ginseng root, food containing Acanthopanax Senticosus Harms)

2] food containing saccharide [oligosaccharide (food containing fluctooligosaccharide, food containing isomaltoligosaccharide, food containing galactooligosaccharide), polysaccharide (food containing Cortinellus shiitake, muco saccharide, food containing protein, food containing chondroitin sulfate, food containing Ganoderma lucidium (Reishi), food containing chitin/chitosan)

3] food containing mineral (food containing calcium, food containing alfalfa, food containing prune extract, food containing β-carotene)

4] food containing fat (fat containing vitamin E [wheat and tear grass germ oil, soybean germ oil, rice germ oil], food containing eicosapentaenoic acid, food containing soybean lecithin, food containing γ-linolenic acid (evening primrose oil, borage oil), food containing docosahexaenoic acid)

5] food containing protein (food containing soybean protein, casein, whey protein, processed carp food)

6] food containing taurine oyster, processed corbicula, processed green sea mussel (7) Others Processed soft-shelled turtle, amino acid dysbolism-oriented food, liquid food (patient's meal)

An administration (taken) amount of the inhibitor of the present invention, which differs owing to an administration method, condition or age of a patient and the like, usually ranges from 0.001 to 3000 mg for one time, preferably from 0.01 to 1000 mg for one to three times a day. The inhibitor of the present invention can be included in these preparation or food products in a ratio of at least 0.01% by weight, preferably from 0.5 to 80% by weight. These preparation or food products may contain other medically efficient components.

EXAMPLES

The present invention is further explained in details based on the examples concretely, but is not limited thereto. In Example, "part(s) by weight" and "% by weight" are referred to as "part(s)" and "%", respectively.

Example 1

To 120 parts of a dried bonito was added 1000 parts of water and the mixture was extracted with hot water at 90° C. for 1 hour and filtered through mesh to give a residue. To 500 parts of the residue (solid content 20%) was added 5 parts of thermolysin enzyme and 900 parts of water. The mixture was adjusted to pH 7.5 with 1% sodium hydroxide and hydrolyzed to digesting rate of 40% at 60° C. for 15 hours. After filtration, 100 parts (E-1) (solid content 40%) of a concentrated solution was obtained.

The concentrated solution was treated with a membrane in the following conditions and 50 parts of a membrane-concentrated fraction (E-2) (solid content 40%) was removed to obtain 50 parts of a membrane-penetrating fraction (E-3) (solid content 40%).

(Membrane Treatment Conditions)
Instrument: CROSS FLOW UF membrane test module (made by Millipore)
Membrane: SEP1013 (fractionation molecular weight 3000, available from Asahi Chemical Industry Co., Ltd.)
Pressurizing condition: Under 1.5 kg/cm$^2$ with nitrogen gas
Linear velocity: 1 m/sec In the above mentioned membrane-penetrating fraction (E-3), it was observed that oligopeptides containing Ile-Tyr (SEQ. ID. NO. 2), Phe-Gln-Pro (SEQ. ID. NO. 3), Ile-Leu-Tyr (SEQ. ID. NO. 4), Ile-Tyr-Ala (SEQ. ID. NO. 5), Ile-Lys-Trp (SEQ. ID. NO. 6), Leu-Lys-Tyr-Pro (SEQ. ID. NO. 7), Ile-Val-Arg-Asp (SEQ. ID. NO. 8), Leu-Lys-Pro-Asn-Met (SEQ. ID. NO. 9), Ile-Trp-His-His-Thr (SEQ. ID. NO. 10), Ala-Leu-Pro-His-Ala (SEQ. ID. NO. 11), Ile-Lys-Pro-Leu-Asn-Tyr (SEQ. ID. NO. 12), Asp-Tyr-Gly-Leu-Tyr-Pro (SEQ. ID. NO. 13). Firstly, a little amount of the above each oligopeptides were synthesized and then was used as each standard samples. The fraction having the same retention time as the standard sample was fractionated using reversed phase high performance liquid chromatography (RP-HPLC). This process was repeated for three times and a sequence of peptide in the fraction having the same retention time was determined using protein sequencer.

An amount of polypeptide having a molecular weight of at least 5000 was 3%.

Angiotensin converting enzyme inhibitory activity in each fraction (E-1, E-2 and E-3) was determined as described below. Assay of angiotensin converting enzyme Inhibitory Activity.

The determination of angiotensin converting enzyme inhibitory activity was performed in accordance with the method of Cheung and Cushman (Biochemical Pharmacology, 20, 1637 (1971)) under the following conditions.
Sbstrate:
  Bz(benzyl)-Gly-His-Leu
  (86 mg digested in 8 ml water-8 ml phosphate buffer
  (500 mM, pH 8.3) containing 1.5 mM NaCl)
Enzyme:
  Rabbit lung acetone powder (available from Sigma)
  (1 g pulverized in 10 ml of mM phosphate buffer pH
  8.3 and centrifuged; the supernatant was used)

One-hundred μl of the above substrate was mixed with 12 μl of enzyme solution and a predetermined amount of the peptide and the mixture was made up with water to make 250 μl. The reaction was conducted at 37° C. for 30 minutes.

The reaction was quenched with 250 μl of 1N—HCl. After completion of the reaction, 1.5 ml of ethyl acetate was added to the reaction mixture and the whole mixture was stirred in a vortex mixer for 15 seconds, after which it was centrifuged. A 1.0 ml aliquot of the ethyl acetate layer was taken and the ethyl acetate was distilled off. The residue was digested in 1 ml of distilled water and the absorbance of extracted hippuric acid was determined at 228 nm ($OD_{228}$).

The inhibitory activity was expressed as the 50% inhibitory concentration [$IC_{50}$(μg/ml)] of the inhibitor (the peptide of the invention) with the $OD_{228}$ value in the absence of the inhibitor being taken as 100% angiotensin converting enzyme activity and the $OD_{228}$ value of the reaction system at reaction time 0 as 0%.

Further, the obtained inhibitor at the following concentration drying was evaluated in terms of the hue, bitterness of 1% solution and taste as follows.

| (Hue) | |
|---|---|
| ⊙ | pure white |
| ○ | almost white |
| △ | slightly yellow |
| × | yellow |

| (Bitterness) | |
|---|---|
| ⊙ | not bitter |
| ○ | a little bitter |
| △ | bitter |
| × | too bitter |

| (Taste) | |
|---|---|
| ⊙ | leave no aftertaste but pleasant taste |
| ○ | leave little aftertaste |
| △ | leave slightly bad aftertaste |
| × | leave bad aftertaste |

TABLE 1

| Fraction | Yield* (%) | $IC_{50}$ (μg/ml) | Hue | Bitterness | Flavor |
|---|---|---|---|---|---|
| E-1 | 33.3 | 80 | △ | △ | × |
| E-2 | 16.7 | 300 | △ | × | × |
| E-3 | 16.7 | 30 | ⊙ | ⊙ | ⊙ |

*Relative value of each fraction based on the weight of the starting material (dried bonito), which is obtained by concentration in dryness.

The component of polypeptide having molecular weight of at least 5000 was 20% in the E-1.

Example 2

To 100 parts of the concentrated solution (E-1) (solid content 40%) obtained in Example 1 was added ethanol at 95% by volume. The mixture was allowed to stand at a room temperature overnight, and a formed precipitate was removed as 85 parts of fraction (E-4) (solid content 40%) by filtration and ethanol in the filtrate was distilled off under reduced pressure to obtain 15 parts of fraction (E-5) (solid content 40%). The above fraction (E-5) comprised all oligopeptide observed in Example 1. The components having a molecular weight of at least 5000 was 5%.

An inhibitory activity was measured in the same manner as in Example 1. Hue, bitterness and taste were evaluated and shown in Table 2.

TABLE 2

| Fraction | Yield* (%) | IC$_{50}$ (μg/ml) | Hue | Bitterness | Flavor |
|---|---|---|---|---|---|
| E-1 | 33.3 | 80 | Δ | Δ | x |
| E-4 | 28.3 | 200 | x | Δ | x |
| E-5 | 5.0 | 40 | ○ | ⊙ | ⊙ |

*Relative value of each fraction based on the weight of the starting material (dried bonito), which is obtained by concentration in dryness.

Example 3

In Example 1, 1000 parts of water were added to 120 parts of the dried bonito to be homogenized. To the resulting mixture were added 5 parts of thermolysin enzyme to hydrolyze in the same manner as in Example 1, and then 100 parts of a concentrated solution (E-6) (solid content 45%) were obtained.

The concentrated solution was treated with a membrane in the same condition as in Example 1 and fifty parts of a membrane-concentrated fraction (E-7) (solid content 45%) was removed to obtain 50 parts of a membrane-penetrating fraction (E-8) (solid content 45%).

The above fraction (E-8) comprised all oligopeptide observed in Example 1. The components having a molecular weight of at least 5000 was 4% in the fraction (E-8).

An inhibitory activity was measured in the same manner as in Example 1. Hue, bitterness and taste were evaluated and shown in Table 3.

TABLE 3

| Fraction | Yield* (%) | IC$_{50}$ (μg/ml) | Hue | Bitterness | Flavor |
|---|---|---|---|---|---|
| E-6 | 37.5 | 110 | x | x | x |
| E-7 | 18.8 | 310 | Δ | x | x |
| E-8 | 18.8 | 35 | ⊙ | ⊙ | ⊙ |

*Relative value of each fraction based on the weight of the starting material (dried bonito), which is obtained by concentration in dryness.

The components having a molecular weight of at least 5000 was 25% in E-6.

Example 4

To 100 parts of the concentrated solution (E-6) (solid content 45%) obtained in Example 1 was added ethanol at 95% by volume. The mixture was allowed to stand at a room temperature overnight, and a formed precipitate was removed as 80 parts of fraction (E-9) (solid content 45%) by filtration and ethanol in the filtrate was distilled off under reduced pressure to obtain 20 parts of fraction (E-10) (solid content 45%). The above fraction (E-10) comprised all oligopeptide observed in Example 1. The components having a molecular weight of at least 5000 was 2% in the fraction (E-10).

An inhibitory activity was measured in the same manner as in Example 1. Hue, bitterness and taste were evaluated and shown in Table 4.

TABLE 4

| Fraction | Yield* (%) | IC$_{50}$ (μg/ml) | Hue | Bitterness | Flavor |
|---|---|---|---|---|---|
| E-6 | 37.5 | 110 | x | x | x |
| E-9 | 30.0 | 200 | Δ | x | x |
| E-10 | 7.0 | 50 | ⊙ | ⊙ | ⊙ |

*Relative value of each fraction based on the weight of the starting material (dried bonito), which is obtained by concentration in dryness.

What is claimed is:

1. A food comprising an angiotensin converting enzyme inhibitor containing a mixture of an oligopeptide having angiotensin converting enzyme inhibitory activity and polypeptides, said mixture being obtained by the steps of:
   digesting a fish meat with thermolysin enzyme to produce a hydrolyzate, and
   treating the hydrolyzate with membrane or by solvent extraction with a polar organic solvent to reduce the content of polypeptides having a molecular weight of at least 5000 to 0.1 to 10% by weight of the total hydrolyzate in the mixture; and
   said oligopeptide having angiotensin converting enzyme inhibitory activity is at least one selected from the group consisting of
   Ile-Tyr-(SEQ. ID. NO. 2),
   Phe-Gln-Pro (SEQ. ID. NO. 3),
   Ile-Leu-Tyr (SEQ. ID. NO. 4),
   Ile-Tyr-Ala (SEQ. ID. NO. 5),
   Ile-Lys-Trp (SEQ. ID. NO. 6),
   Leu-Lys-Tyr-Pro (SEQ. ID. NO. 7),
   Ile-Val-Arg-Asp (SEQ. ID. NO. 8),
   Leu-Lys-Pro-Asn-Met (SEQ. ID. NO. 9),
   Ile-Trp-His-His-Thr (SEQ. ID. NO. 10),
   Ala-Leu-Pro-His-Ala (SEQ. ID. NO. 11),
   Ile-Lys-Pro-Leu-Asn-Tyr (SEQ. ID. NO. 12),
   Asp-Tyr-Gly-Leu-Tyr-Pro (SEQ. ID. NO. 13), and
   Ile-Val-Gly-Arg-Pro-Arg-His-Gln-Gly (SEQ. ID. NO. 14).

2. The food of claim 1, wherein the fish meat is a dried fish meat.

3. The food of claim 2, wherein the dried fish is a dried bonito.

* * * * *